(12) United States Patent
Kador

(10) Patent No.: US 8,877,766 B2
(45) Date of Patent: Nov. 4, 2014

(54) NEUROPROTECTIVE MULTIFUNCTIONAL ANTIOXIDANTS AND THEIR MONOFUNCTIONAL ANALOGS

(71) Applicant: Peter F. Kador, Omaha, NE (US)

(72) Inventor: Peter F. Kador, Omaha, NE (US)

( * ) Notice: Subject to any disclaimer, the term of this patent is extended or adjusted under 35 U.S.C. 154(b) by 21 days.

(21) Appl. No.: 13/769,247

(22) Filed: Feb. 15, 2013

(65) Prior Publication Data

US 2014/0235858 A1    Aug. 21, 2014

(51) Int. Cl.
| | | |
|---|---|---|
| *C07D 401/04* | (2006.01) | |
| *C07D 239/60* | (2006.01) | |
| *A61K 31/505* | (2006.01) | |
| *C07D 239/52* | (2006.01) | |
| *C07D 403/04* | (2006.01) | |
| *C07D 239/47* | (2006.01) | |
| *C07D 239/42* | (2006.01) | |

(52) U.S. Cl.
CPC ........... *C07D 403/04* (2013.01); *C07D 239/60* (2013.01); *C07D 401/04* (2013.01); *C07D 239/52* (2013.01); *C07D 239/47* (2013.01); *C07D 239/42* (2013.01)
USPC ........... 514/269; 514/275; 544/298; 544/320; 544/330; 544/332

(58) Field of Classification Search
USPC ........... 544/298, 320, 330, 332; 514/269, 275
See application file for complete search history.

(56) References Cited

U.S. PATENT DOCUMENTS

| | | | |
|---|---|---|---|
| 4,711,888 | A | 12/1987 | Walker et al. |
| 5,071,852 | A | 12/1991 | Walker |
| 5,302,597 | A | 4/1994 | Connor et al. |
| 7,547,709 | B2 | 6/2009 | Pratt et al. |
| 8,268,849 | B2 | 9/2012 | Kador et al. |
| 2008/0227776 | A1 | 9/2008 | Oates et al. |
| 2010/0041683 | A1 | 2/2010 | Pratt et al. |

FOREIGN PATENT DOCUMENTS

| | | |
|---|---|---|
| WO | WO 2005/105966 | 11/2005 |
| WO | WO 2009/144253 | 12/2009 |
| WO | WO 2012/007861 | * 1/2012 |

OTHER PUBLICATIONS

Zaidi et al., CAPLUS Abstract 120:93935 (1994).*
Bundgaard, Design of Prodrugs, p. 1, 1985.*
Wolff, Some consideration for prodrug design, Burgers Medicinal Chemistry and Drug Discovery, 5th Edition, vol. I: Principles and Practice, pp. 975-977, 1995.*
Banker et al., Prodrugs, Modern Pharmaceutics, Third Edition, Revised and Expanded, pp. 451 & 596 (1996).*
Silverman, Prodrugs and Drug Delivery Systems, The Organic Chemistry of Drug Design and Drug Action, pp. 352-400 (1992).*
Jin et al., "Multifunctional Antioxidants for the Treatment for Age Related Diseases", Journal of Medicinal Chemistry, Feb. 11, 2010, 53(3), 1117-1127.
Zaidi et al., "Transition Metal Complexes of 2-(N-Succinimidyl)Pyrimidine", Synthesis and Reactivity in Inorganic and Metal-Organic Chemistry, 1993, 23(9), 1571-1584.

* cited by examiner

*Primary Examiner* — Deepak Rao
(74) *Attorney, Agent, or Firm* — Richard C Litman

(57) ABSTRACT

The neuroprotective multifunctional antioxidants are compounds that contain a 2-diacetylamino-5-hydroxypyrimidine moiety, having the structural formula:

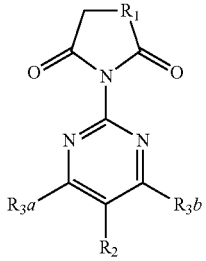

wherein $R_1$ is $CH_2$ or $C_2H_4$; $R_2$ is H or —$OR_4$ where $R_4$ is H or aryl; and $R_{3a}$ and $R_{3b}$ are independently selected from the group consisting of H and —O-alkyl. The antioxidants are orally bioavailable metal-attenuating multifunctional antioxidants that can independently attenuate transition metals, as well as scavenger free radicals. The multifunctional antioxidant compounds, by their ability to independently chelate metals, such as Fe, Cu or Zn, and scavenge free radicals generated from different sources, are neuroprotective and are beneficial for the treatment of various neurological disorders, such as Alzheimer's disease, Parkinson's disease, ALS, traumatic brain injury, ocular disorders, such as cataract, glaucoma, age-related macular degeneration and other retinal degeneration, as well as for reducing the progression of diabetic complications.

13 Claims, 7 Drawing Sheets

HK-1

HK-2

HK-3

HK-4

HK-5

HK-6

HK-7

HK-8

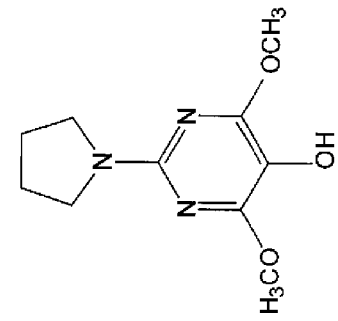
HK-9
*Fig. 2A*
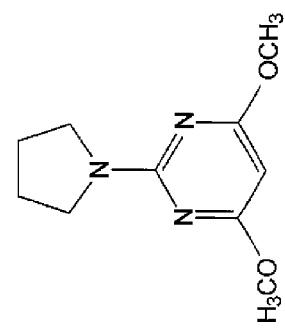
HK-10
*Fig. 2B*
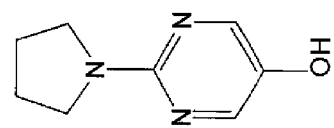
HK-11
*Fig. 2C*
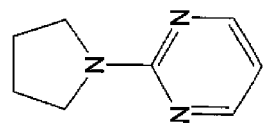
HK-12
*Fig. 2D*
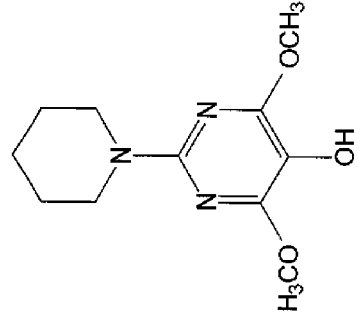
HK-13
*Fig. 2E*
HK-14
*Fig. 2F*
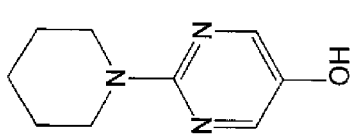
HK-15
*Fig. 2G*
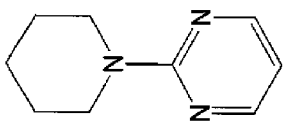
HK-16
*Fig. 2H*

| Compound | Fe$^{2+}$ | Fe$^{3+}$ | Cu$^+$ | Cu$^{2+}$ | Zn$^{2+}$ | Mg$^{2+}$ | Ca$^{2+}$ |
|---|---|---|---|---|---|---|---|
| HK-1 | 1:2.1 | 1:2.0 | 1:2.0 | 1:2.3 | 1:1.9 | 0* | 0* |
| HK-2 | 1:2.1 | 1:2.0 | 1:2.0 | 1:2.3 | 1:1.9 | 0* | 0* |
| HK-3 | 1:2.0 | 1:2.1 | 1:1.9 | 1:2.0 | 1:2.1 | 0* | 0* |
| HK-4 | 1:2.0 | 1:2.1 | 1:2.0 | 1:2.1 | 1:2.0 | 0* | 0* |
| HK-5 | 1:2.1 | 1:1.8 | 1:1.9 | 1:2.0 | 1:2.2 | 0* | 0* |
| HK-6 | 1:1.9 | 1:1.9 | 1:1.9 | 1:1.8 | 1:2.0 | 0* | 0* |
| HK-7 | 1:2.0 | 1:2.1 | 1:1.9 | 1:2.0 | 1:2.1 | 0* | 0* |
| HK-8 | 1:2.0 | 1:1.8 | 1:2.0 | 1:1.9 | 1:2.1 | 0* | 0* |

The stoichiometry of complex of HK analogs and metal ion.*
*No intersection in Job's plot

Fig. 7

NEUROPROTECTIVE MULTIFUNCTIONAL ANTIOXIDANTS AND THEIR MONOFUNCTIONAL ANALOGS

BACKGROUND OF THE INVENTION

1. Field of the Invention

The present invention relates to antioxidants, and particularly to neuroprotective multifunctional antioxidants that can both chelate metals, such as Fe, Cu or Zn, and scavenge free radicals. The invention also relates to antioxidant monofunctional analogs of the neuroprotective multifunctional antioxidant compounds. The compounds can be administered orally, and can cross the blood-brain barrier, so that the compounds are beneficial for the treatment of various neurological disorders, such as Alzheimer's disease, Parkinson's disease, ALS (amyotrophic lateral sclerosis), traumatic brain injury, ocular disorders such as cataract, glaucoma, age-related macular degeneration and other retinal degeneration, as well as reducing the progression of diabetic complications.

2. Description of the Related Art

Oxidative damage is a hallmark of neurodegenerative disorders. Oxidative stress results from reactive oxygen species (ROS) that damage cellular components by oxidizing proteins, lipid bilayers and DNA. This results in altered protein conformations, reduced enzyme activities, lipid peroxide generation that disrupts plasma and organelle membranes, and altered DNA, which leads to strand breaks, DNA-protein cross-linking, and mutations through base modifications. ROS includes the super oxide anion ($O_2^-$), the hydroxyl radical (—OH), singlet oxygen ($^1O_2$), and hydrogen peroxide ($H_2O_2$). Superoxide anions continuously form in mitochondria, as molecular oxygen ($O_2$) acquires an additional electron. Hydroxyl radicals, the most reactive and damaging of generated ROS, predominantly form by a Fenton reaction between hydrogen peroxide and redox active transition metals, such as iron and copper. Although these metals are oxidized during this process, they are returned to their "active" (reduced) state through a process of "redox cycling" with vitamin C or other cellular reductants. Hydrogen peroxide, produced in vivo through several reactions, can either be converted to the highly reactive and damaging hydroxyl radicals, or converted to water It is formed by the reduction of superoxide radical by superoxide dismutase and reduced to water by either catalase or glutathione peroxidase.

Oxidative stress increases with age, and prolonged exposure of tissues to oxidative stress results in cellular damage that eventually leads to cell death. ROS activity has been observed in the hippocampus, substantia nigra and caudate putamen of the brain and in the spinal fluid. Neural tissues in the brain are especially susceptible to ROS because of the higher metabolic rates, high compositions of peroxidation susceptible fatty acids, high intracellular concentrations of transition metals capable of catalyzing Fenton reactions, low levels of antioxidants, and reduced capability for tissue regeneration. Neural tissues also possess brain-specific oxidases, such as monoamine oxidase, that can generate hydrogen peroxide. Neuroinflammatory responses induced by reactive microglia, macrophages and proinflammatory T-cells can also generate ROS.

In the brain, the redox-active metals iron (Fe), copper (Cu), and zinc (Zn) accumulate with age, and this accumulation is linked to altered brain metabolism and increased amyloid precursor protein (APP) expression. Amyloid beta (Aβ) is the major proinflammatory component of Alzheimer's disease (AD) plaques, and its binding to Cu, Fe, and Zn promotes Aβ aggregation into protease-resistant, metal-enriched precipitates. Aβ efficiently generates reactive oxygen species in the presence of copper and iron. Aberrant biometal homeostasis and metalloprotein reactions occur during the development of AD and results in oxidation-linked neurodegeneration.

The age-dependent accumulation of Fe also alters Fe metabolism in the brain in AD and Parkinson's disease (PD), which has been linked to changes in the expression of lactotransferrin receptor, melanotransferrin, ceruloplasmin and divalent cation transporters in brain ion transport. Increased Fe levels have also been observed in pathologically affected areas of postmortem brains in other neurodegenerative diseases, such as Parkinson's patients, and these areas correspond to an increased severity of neuropathological changes. Changes in Cu levels can also affect the brain by interfering with Fe. The Cu-binding enzyme ceruloplasmin represents a link between Cu and Fe metabolism because this enzyme regulates the Fe redox state through its ferroxidase activity by converting Fe (II) to Fe (III). Ceruloplasmin is rapidly degraded when Cu is not properly incorporated into the protein at the rate of the protein synthesis, as seen in aceruloplasminemia, where altered Fe hemostasis occurs with marked Fe accumulation into neuroglia and neurons. In AD patients, a decreased neuronal induction of ceruloplasmin may lead to an accumulation of redox-active iron in neurons.

Targeting oxidative pathways associated with neurodegeneration can be therapeutic. Reducing ROS with free radical scavenging antioxidants ranging from natural products (curcumin, melatonin, resveratrol, *Ginkgo biloba* extract, green tea, vitamin C, L-carnitine, vitamin E, and cannabinoids) to lipoic acid derivatives, Coenzyme Q (MitoQ) analogs, and "thiol-delivering" glutathione-mimics have been reported. However, the ability of most of these compounds to cross the blood-brain barrier (BBB) has not been demonstrated.

ROS can also be reduced through the use of biometal attenuating compounds. Desferoxamine (desferrioxamine) can bind Fe, Cu, and Zn and decrease AD progression. However, desferoxamine is not orally active and does not significantly cross the BBB. DdP109, a more lipophilic chelator, has been reported to reduce the levels of aggregated insoluble Aβ and increase its soluble forms when administered to transgenic mice. The orally active metal chelator clioquinol (PBT1), which modulates the Fenton reaction, decreases Cu uptake in the brain, disaggregates redox metal-induced Aβ aggregation, and retards fibril growth, shows efficacy in both animals and several clinical trials. Oral PBT2 also reduces Aβ aggregation and toxicity by interfering with the redox activity associated with Aβ-metal complexes. PBT2 significantly reduces Aβ concentrations in the brain and rapidly reversed cognitive deficits as demonstrated in a Phase IIa clinical trial, where AD patients improved in two neuropsychological tests. These results support the premise that attenuation of metal-protein interactions is a promising strategy for therapeutic intervention.

Iron can be released from hemoglobin during traumatic brain injury (TBI) or hemorrhagic stroke. The increase in free ferrous iron can lead to oxidative damage. Children are especially vulnerable to TBI induced hemorrhage and cell death because their immature brain has a muted response to oxidative stress due to inadequate expression of certain antioxidant molecules, and their developing brain is less able to detoxify free iron. TBI also elicits an acute inflammatory response in which ROS is generated. Anti-inflammatory agents, antioxidants, and the iron chelator desferoxamine have been proposed to treat the increased inflammation, oxidative stress and presence of free iron levels observed in adult and pediatric TBI.

Age-related macular degeneration (AMD) risk factors, such as smoking, suggest that AMD is linked to oxidative stress. A role for oxidative stress in AMD is supported by the AREDS trial results, which found that antioxidants and zinc reduce the risk of AMD progression, as well as oxidative stress-induced endothelial dysfunction, by reducing ROS. Patients with AMD have higher retinal levels of lipid peroxidation products, which are present in drusen. The retina is vulnerable to oxidative stress because of its high levels of oxygen that are required for retinal function. Moreover, the membranes of rods and cones in the outer nuclear layer (ONL) contain a high percentage of polyunsaturated fatty acids that are susceptible to lipid peroxidation. The macular region is particularly susceptible to ROS because incoming light is focused onto the macula. Incoming light is a constant source of oxidative stress because photo-oxidation generates ROS. ROS is also generated by retinal pigmented epithelial (RPE) cell phagocytosis and the photosensitizing activity of lipofuscin. Exposing RPE cells to ROS leads to apoptosis and premature senescence Aβ deposition is also present in AMD. Drusen, a biomarker for AMD that forms adjacent to the RPE, contains Aβ, whose presence has been linked to local inflammatory events. As the major pro-inflammatory component of AD plaques, retinal Aβ has been linked to RPE dysfunction that results in retinal degeneration and AMD. In RPE, Aβ accumulation also affects the balance between vascular endothelial growth factor (VEGF) and pigment epithelium-derived factor (PEDF).

Several animal models show AMD-like retinal changes that are linked to oxidative stress, iron dysregulation, and Fenton chemistry. These include the C57BL/6 mice exposed to cigarette smoke, mice deficient in SOD1, knockout mice (DKO) deficient in ceruloplasmin (Cp) and its homolog hephaestin, and RCS rats. Introducing iron directly into the eye also produces retinal degeneration.

Targeting oxidative pathways associated with AMD-linked retinal changes shows therapeutic potential. The AREDS antioxidant formulation reduces the risk of AMD progression to the advanced stage by 25%. Antioxidants also reduce oxidative stress in cultured RPE cells. Addition of bovine melanosomes or melatonin to non-pigmented bovine RPE also reduces the photosensitized and iron-mediated oxidation of RPE cells. The antioxidant N-tert-butyl hydroxylamine (Nt-BHA), when added to iron-overloaded human RPE, reduces ROS and maintains GSH levels. Similarly, treatment with salicylaldehyde isonicotinyl hydrazone (SIH) protects RPE cells against the Fenton-generated hydroxyl radicals. The antioxidant quercetin also protects RPE against hydrogen peroxide-induced oxidative stress. Free radical scavengers, such as N-acetylcysteine, dimethylthiourea, *Ginkgo biloba* extract, phenyl-N-tert-butylnitrone, WR-77913, Tempol H, and edaravone, protect against light-induced retinal degeneration. Retinal degeneration in DKO mice is reduced with the iron chelator deferiprone. Administration of the multifunctional antioxidant JHX-4 also protects rats against light-induced retinal damage by reducing biomarkers of oxidative stress in the neural retinas, preservation of retinal ERG patterns, and preservation of the photoreceptor layer.

In addition to AMD, iron-associated oxidative injury plays a role in retinal degenerations, such as retinitis pigmentosa. Zinc-deferoxamine has been known to attenuate retinal degeneration in the rd10 mouse model of retinitis pigmentosa.

Increased mRNA and protein levels for the iron-regulating proteins transferrin, ceruloplasmin, and ferritin are present in glaucoma. By inducing lysosomal membrane permeabilization and the release of cathepsin D into the cytosol, ROS leads to trabecular meshwork (TM) cell death. This cell death is reduced by chelation. Lysosomes degrade organelles, long-lived proteins, and extracellular and membrane-bound materials. Significant concentrations of labile iron can accumulate within lysosomes because of their breakdown of iron-containing endocytosed and autophagocytosed materials. This can result in lysosomal hydroxyl radicals being generated through Fenton reactions. Neuroprotection by iron chelators prevents hydroxyl radical formation in the Fenton reaction by sequestering redox-active iron. Iron chelators can also upregulate or stabilize hypoxia-inducible factor-1a (HIF-1a). The stability of HIF-1a is controlled by iron-dependent oxygen-sensor enzymes, HIF prolyl-4-hydroxylases (PHDs) that target HIF-1a for degradation. HIF-1a is present in the glaucomatous retina and has been linked to RGC death. The HIF system is an emerging target for neuroprotection because it promotes the stabilization of bHIF-1a and increases transcription of HIF-1-related survival genes. Iron chelators appear to provide neuroprotection by inhibiting PHDs that target the HI"F-1 signaling pathway and ultimately activate the HIF-1-dependent neuroprotective genes.

Cataracts linked to oxidative stress and ROS include those associated with aging, ionizing and UV radiation, increased oxygen tension resulting from vitrectomy surgery, and tobacco smoke. In many of these cataracts, the Fenton reaction contributes to ROS because Cu and Fe also accumulate in lenses with aging and exposure to tobacco smoke. In AD patients, Aβ deposition also causes cataracts by accumulating as electron-dense deposits in the cytoplasm of supranuclear/deep cortical lens fibers cells. Aβ deposits similarly occur in Aβ transgenic mice, where they can be reduced by chelation.

In cataracts, antioxidants have been widely used to reduce cataract formation in experimental animals. Chelation reduces Aβ deposition observed clinically and experimentally in mice. Chelation also reduces cataracts in β-thalassemia patients, and in tobacco smoke-exposed rats.

Cellular exposure to ionizing radiation can alter atomic structures through either direct interactions of the radiation with target macromolecules, or indirectly through the generation of ROS by water radiolysis. Moreover, the oxidative damage may spread from the targeted to neighboring, non-targeted bystander cells through redox-modulated intercellular mechanisms. Radiation can also initiate the release of iron via the photoreduction of iron stored inside ferritin.

Chelation of Cu, Fe, Mn, and Zn facilitates the tissue repair processes required for recovery from radiation injury, including survival of lethally irradiated mice and rats. Iron chelators may also help prevent photo-aging. Administration of the multifunctional antioxidant JHX-4 to Long-Evans rats that were administered 15 Gy of whole head gamma irradiation significantly delayed cataract formation, in addition to partially alleviating a reduction in weight loss due to apparent salivary gland response to irradiation.

Oxidative stress is also one of the major causative factors for diabetes and diabetic complications, and increased heme iron has been significantly associated with an increased risk of insulin resistance and type-2 diabetes. Experimentally, antioxidants and chelators have been observed to be beneficial in the treatment of nerve and vascular dysfunction in experimental diabetes. Administration of the multifunctional antioxidant JHX-4 to diabetic rats also delayed the progression of cataracts.

Thus, neuroprotective multifunctional antioxidants solving the aforementioned problems is desired.

SUMMARY OF THE INVENTION

The neuroprotective antioxidant compounds have the formula:

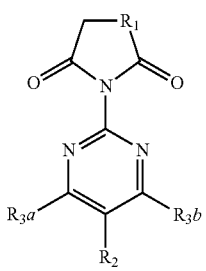

wherein $R_1$ is $CH_2$ or $C_2H_4$; $R_2$ is H or $—OR_4$ where $R_4$ is H, carbonylalkyl or carbonylaryl; and $R_{3a}$ and $R_{3b}$ are independently selected from the group consisting of H and $—O$-alkyl or a pharmaceutically acceptable salt thereof. When $R_2$ is a hydroxyl group (OH), the compounds exhibit multifunctional activity, i.e., the compounds exhibit neuroprotective activity by their ability to independently chelate metals (such as Fe, Cu or Zn) and to scavenge free radicals generated from different sources. The monofunctional analogs of the multifunctional antioxidants, when $R_2$ is hydrogen, exhibit neuroprotective antioxidant activity only by chelating metals, such as Fe, Cu or Zn, that might otherwise contribute to the formation of ROS.

An additional class of structurally similar neuroprotective antioxidant compounds that are structural analogs of the first group have the formula

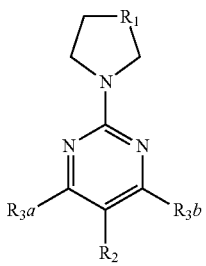

wherein $R_1$ is $CH_2$ or $C_2H_4$; $R_2$ is H or $—OR_4$ where $R_4$ is H, carbonylalkyl or carbonylaryl; and $R_{3a}$ and $R_{3b}$ are independently selected from the group consisting of H and $—O$-alkyl or a pharmaceutically acceptable salt thereof. These compounds are effective for scavenging free radicals, and can also be used for treatment of neurological diseases that mediate tissue damage, at least in part, through reactive oxygen species (ROS).

The multifunctional compounds, by their ability to independently chelate metals (such as Fe, Cu or Zn) and to scavenge free radicals generated from different sources and their monofunctional analogs, are neuroprotective, and are beneficial for the treatment of various neurological disorders, such as Alzheimer's disease, Parkinson's disease, ALS (amyotrophic lateral sclerosis), traumatic brain injury, ocular disorders (such as cataract, glaucoma, age-related macular degeneration and other retinal degeneration), as well as for reducing the progression of diabetic complications. These compounds may also be beneficial in reducing the accumulation of Fe, Cu, or Zn metals in select diseases.

These and other features of the present invention will become readily apparent upon further review of the following specification and drawings.

BRIEF DESCRIPTION OF THE DRAWINGS

FIG. 2A is a representative nonfunctional parent compound according to the present invention.

FIG. 2B is another representative neuroprotective monofunctional antioxidant according to the present invention FIG. 2C is another representative nonfunctional parent compound according to the present invention.

FIG. 2D is another representative neuroprotective monofunctional antioxidant according to the present invention.

FIG. 2E is another representative nonfunctional parent compound according to the present invention FIG. 2F is another representative neuroprotective monofunctional antioxidant according to the present invention.

FIG. 2G is another representative nonfunctional parent compound according to the present invention.

FIG. 2H is another representative neuroprotective monofunctional antioxidant according to the present invention.

FIG. 7 shows Table 1 the stoichiometry of the complex of HK analogs (the neuroprotective multifunctional antioxidants and their analogs according to the present invention) and various metal ions that can be chelated by the analogs.

DETAILED DESCRIPTION OF THE PREFERRED EMBODIMENTS

Figure 1A:
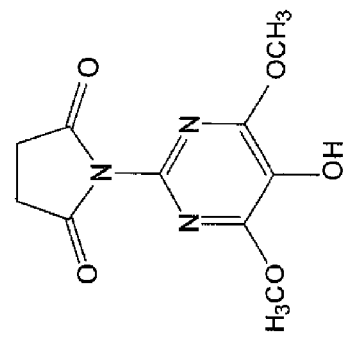
FIG. 1A is a representative neuroprotective monofunctional antioxidant according to the present invention.
Figure 1B:
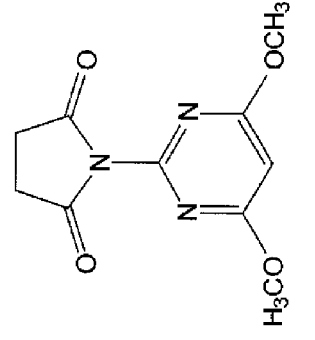
FIG. 1B is a representative neuroprotective multifunctional antioxidant according to the present invention
Figure 1C:
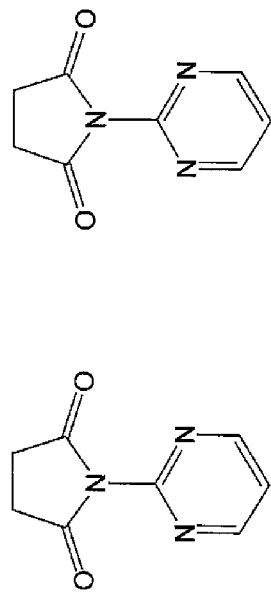
FIG. 1C is another representative neuroprotective monofunctional antioxidant according to the present invention.
Figure 1D:
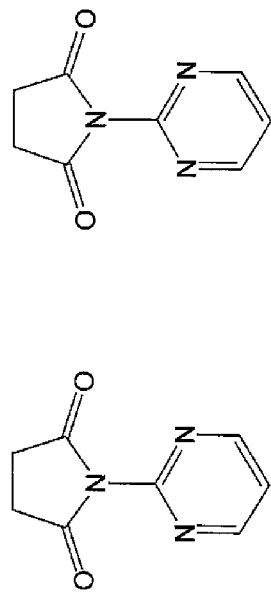
FIG. 1D is another representative neuroprotective multifunctional antioxidant according to the present invention.
Figure 1E:
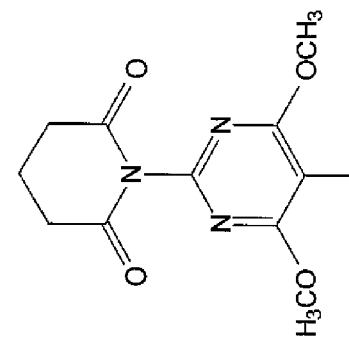
FIG. 1E is another representative neuroprotective monofunctional antioxidant according to the present invention
Figure 1F:
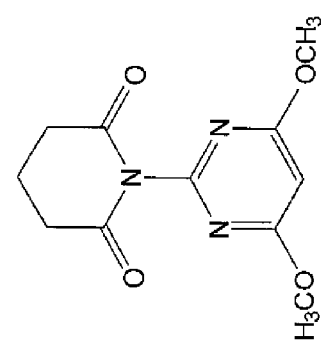
FIG. 1F is another representative neuroprotective multifunctional antioxidant according to the present invention.
Figure 1G:
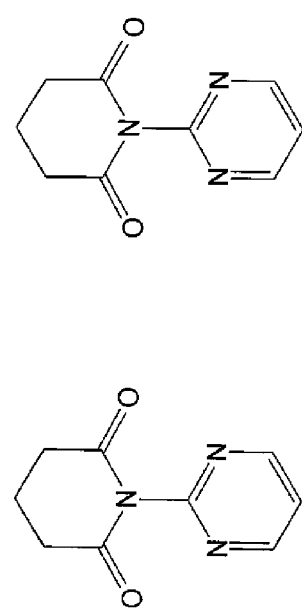
FIG. 1G is another representative neuroprotective monofunctional antioxidant according to the present invention.
Figure 1H:
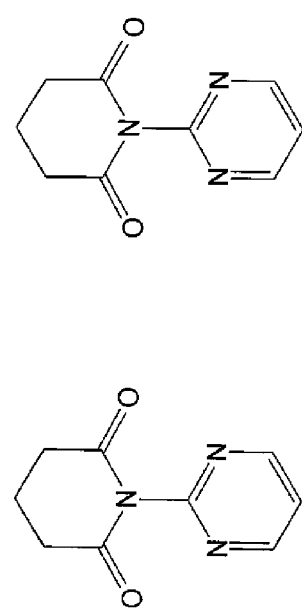
FIG. 1H is another representative neuroprotective multifunctional antioxidant according to the present invention.

The neuroprotective antioxidant compounds have the general formula:

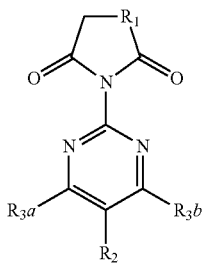

wherein $R_1$ is $CH_2$ or $C_2H_4$; $R_2$ is H or $—OR_4$ where $R_4$ is H, carbonylalkyl or carbonylaryl; and $R_{3a}$ and $R_{3b}$ are independently selected from the group consisting of H and —O-alkyl or a pharmaceutically acceptable salt thereof. When $R_2$ is a hydroxyl group (OH), the compounds exhibit multifunctional activity, i.e., the compounds exhibit neuroprotective activity by their ability to independently chelate metals (such as Fe, Cu or Zn) and to scavenge free radicals generated from different sources. The monofunctional analogs of the multifunctional antioxidants, when $R_2$ is hydrogen, exhibit neuroprotective antioxidant activity only by chelating metals, such as Fe, Cu or Zn, that might otherwise contribute to the formation of ROS.

An additional class of structurally similar neuroprotective antioxidant compounds that are structural analogs of the first group have the formula

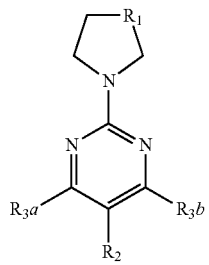

wherein $R_1$ is $CH_2$ or $C_2H_4$; $R_2$ is H or $—OR_4$ where $R_4$ is H, carbonylalkyl or carbonylaryl; and $R_{3a}$ and $R_{3b}$ are independently selected from the group consisting of H and —O-alkyl or a pharmaceutically acceptable salt thereof. These compounds with $—OR_4$ are effective for scavenging free radicals, and can also be used for treatment of neurological diseases that mediate tissue damage, at least in part, through reactive oxygen species (ROS).

The term "alkyl," as employed herein, includes linear, branched, and cyclic (see cycloalkyl below) chain hydrocarbons containing about 1 to 10 carbons, preferably 1 to 8 carbons, more preferably 1 to 4 carbons (a "lower alkyl"), in the normal chain. An alkyl may be referred to as a hydrocarbyl. Examples of suitable alkyl groups include methyl, ethyl, propyl, isopropyl, butyl, t butyl, isobutyl, pentyl, hexyl, isohexyl, heptyl, 4,4 dimethylpentyl, octyl, 2,2,4 trimethylpentyl, nonyl, decyl, the various branched chain isomers thereof, and the like. Each alkyl group may optionally be substituted with 1 to 4 substituents, which include, for example, halo (such as F, Cl, Br, I), haloalkyl (such as $CCl_3$ or $CF_3$), alkyl, alkoxy, hydroxy, aryl, aryloxy, aralkyl, cycloalkyl, alkylamino, alkanoylamino, oxo, acyl, arylcarbonylamino, amino (—NH2), substituted amino, nitro, cyano, carboxy (—COOH), carbonyl (—C(═O)), epoxy, urea (—NH-CONH$_2$), thiol (—SH), alkylthio, alkyloxycarbonyl (—C(═0)-0R), alkylcarbonyloxy (—OC(═O)—R), carbamoyl (NH2C(═0)- or NHRC(═O)—), and/or alkylurea (—NH-CONHR), wherein R in the aforementioned substituents represents an alkyl radical. The alkyl group may optionally comprise one or more carbon-to-carbon double bonds (i.e., the alkyl group may be unsaturated). The alkyl may also comprise at least one (e.g., from 1 to about 4) sulfur, oxygen, or nitrogen heteroatoms within the hydrocarbon chain. For example, the alkyl can be —OR, —SR, or —NHR, wherein R is a hydrocarbon chain.

The term "cycloalkyl," as employed herein, includes saturated or unsaturated cyclic hydrocarbon groups containing 1 to 3 rings, that is, monocyclic alkyl, bicyclic alkyl and tricyclic alkyl. Cycloalkyl groups may contain a total of 3 to 20 carbons forming the ring(s), preferably 3 to 10 carbons forming the ring(s), and may optionally be fused to 1 or 2 aromatic rings, as described below for "aryl". Unsaturated cycloalkyl groups may contain one or more double bonds and/or triple bonds. Cycloalkyl groups include, without limitation, cyclopropyl, cyclobutyl, cyclopentyl, cyclohexyl, cycloheptyl, cyclooctyl, cyclodecyl and cyclododecyl, cyclopentenyl cyclohexenyl, cycloheptenyl, cyclooctenyl, cyclohexadienyl, and cycloheptadienyl. Each cycloalkyl group may be optionally substituted with substituents, such as halogen, alkyl, alkoxy, hydroxy, aryl, aryloxy, aralkyl, cycloalkyl, alkylamido, alkanoylamino, oxo, acyl, arylcarbonylamino, amino, substituted amino, nitro, cyano, thiol and/or alkylthio.

The term "aryl," as employed herein, refers to monocyclic and bicyclic aromatic groups containing 6 to 10 carbons in the ring portion. Examples of aryl groups include, without limitation, phenyl or naphthyl, such as 1-naphthyl and 2-naphthyl, or indenyl. Aryl groups may optionally include one to three additional rings fused to a cycloalkyl ring or a heterocyclic ring. Aryl groups may be optionally substituted through available carbon atoms with 1, 2, or 3 groups selected from hydrogen, halo, alkyl, polyhaloalkyl, alkoxy, alkenyl, trifluoromethyl, trifluoromethoxy, alkynyl, aryl, heterocyclo, aralkyl, aryloxy, aryloxyalkyl, aralkoxy, arylthio, arylazo, heterocyclooxy, hydroxy, nitro, cyano, sulfonyl anion, amino, or substituted amino.

The terms "halogen," "halo," and "halide" refer to chlorine, bromine, fluorine or iodine.

The term "multifunctional", as used herein, means that the compound can both chelate metals, such as Fe, Cu or Zn, and scavenge free radicals, thereby helping to prevent or inhibit the formation of reactive oxygen species (ROS) that might otherwise form by reaction with the metal, and also scavenging free radicals directly by converting ROS to less harmful forms.

Representative neuroprotective multifunctional antioxidants and their monofunctional analogs are compounds HK-1 to HK-8, as shown in FIGS. 1A to 1H. Compounds HK-1 to HK-8 can be synthesized from the 2-aminopyrimidines 19, 20, 21 and 22 by coupling with commercially available succinic anhydride 17 or glutaric anhydride 18, followed by hydrogenation, as shown in the reaction scheme of FIG. 2. The aminopyrimidines 19 and 20 (FIG. 3) were obtained as previously described in Kador, P et al., *Multifunctional Antioxidants and Methods of Use Thereof*, U. P. Office, Editor 2012, Board of Regents of the University of Nebraska: USA, p. 33.

Compound 21 (FIG. 3) is commercially available. Compound 22 can be obtained from commercially available 2-chloro-4,6-dimethoxypyrimidine by nucleophilic substitution of the 2-chloride atom with benzylamine, followed by hydrogenation, as shown in the reaction scheme of FIG. 4.

The following examples illustrate the preparation of the neuroprotective multifunctional and monofunctional antioxidants.

Example 1

N-benzyl-4,6-dimethoxypyrimidin-2-amine

Compound 28

A mixture of 2-chloro-4,6-dimethoxypyrimidine (27) (50.0 g, 0.29 mol), $BnNH_2$ (93.3 mL, 0.85 mol) and $K_2CO_3$ (2.5 g, 0.45 mol) in dioxane (1.0 L) was refluxed for 4 days.

The reaction was filtered and the filtrate concentrated in vacuo to give a yellow oil, which after silica gel column chromatography with 20:1 to 10:1 hexanes:EtOAc gave 61.7 g (87%) of white solid 28. $^1$H NMR (CDCl$_3$) δ 7.36-7.27 (m, 5H), 5.42 (s, 1H), 5.25 (s, 1H), 4.61 (d, J=5.86 Hz, 2H), 3.83 (s, 6H).

Example 2

2-amino-4,6-dimethoxypyrimidine

Compound 22

Compound 28 (27.0 g, 0.11 mol) in 400 mL of MeOH was hydrogenated for 2 days r.t. in the presence of 5.4 g of 20% Pd(OH$_2$) catalyst. After filtration, and solvent evaporation, a white solid was obtained which after silica gel column chromatography using 50:1 CHCl$_3$:MeOH yielded 16.8 g*98%) of 22. $^1$H NMR (CDCl$_3$) δ 5.47 (s, 1H, 4.90 (s, 2H), 3.84 (s. 6H).

Example 3

Synthesis of HK-1, HK-3, HK-5, and HK-7

The following describes the general synthesis of 1-(2-pyrimidyl)pyrrolidine-2,5-dione (HK-1), 1-(4,6-dimethoxy-2-pyrimidyl)pyrrolidine-2,5-dione (HK-3), 1-(2-pyrimidyl)piperidine-2,6-dione (HK-5), 1-(4,6-dimethoxy-2-pyrimidyl) piperidine-2,6-dione (HK-7), 1-(5-benzyloxy-2-pyrimidyl) pyrrolidine-2,5-dione (Compound 23), 1-(5-benzyloxy-2-pyrimidyl)piperidine-2,6-dione (Compound 24), 1-(4,6-dimethoxy-5-benzyloxy-2-pyrimidyl)pyrrolidine-2,5-dione (Compound 25), and 1-(4,6-dimethoxy-5-benzyloxy-2-pyrimidyl)piperidine-2,6-dione (Compound 26).

Figure 3:
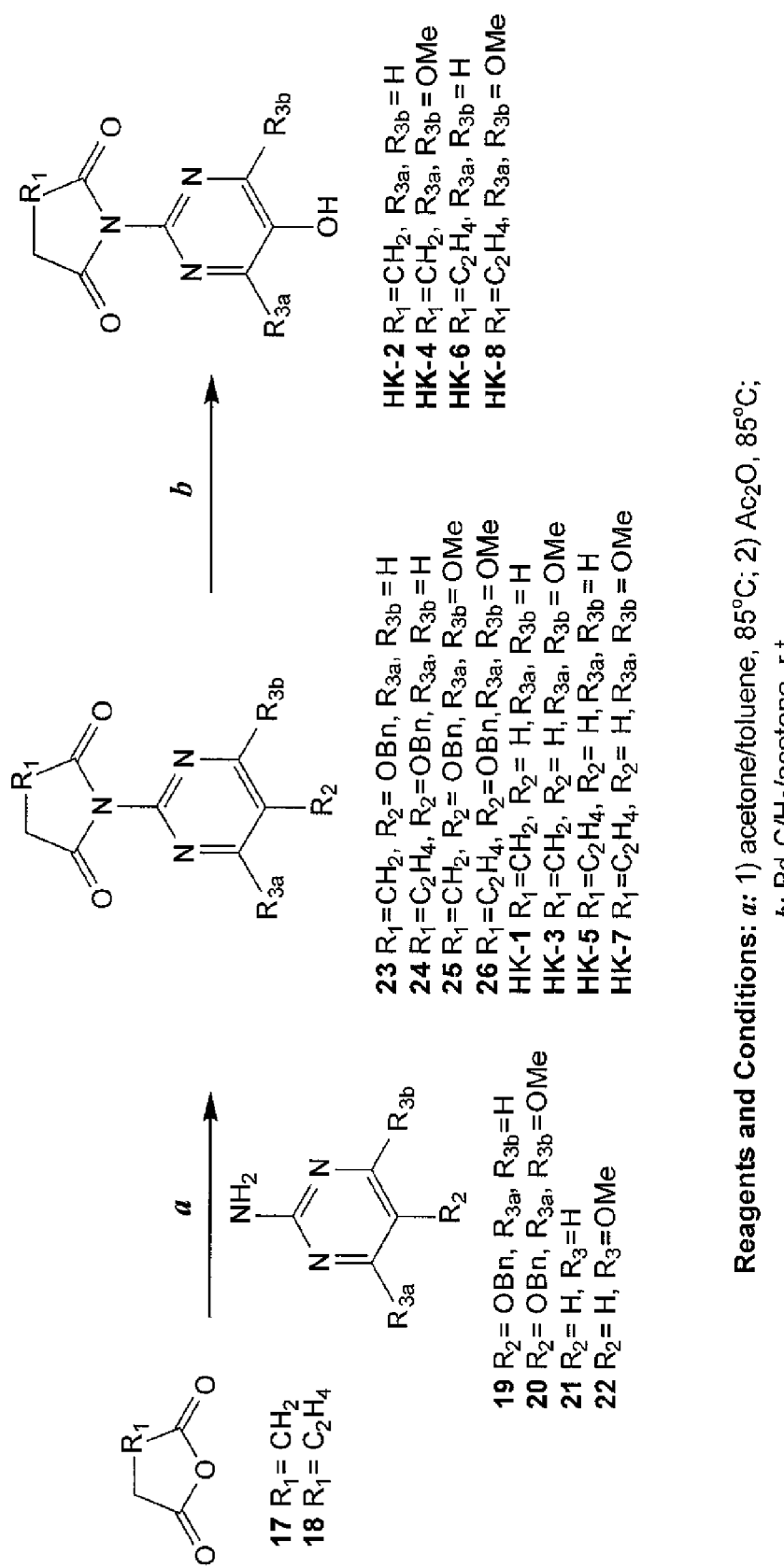
FIG. 3 is a reaction scheme showing the synthesis of the neuroprotective multifunctional and monofunctional antioxidants HK-1 to HK-8 according to the present invention.
Figure 4:
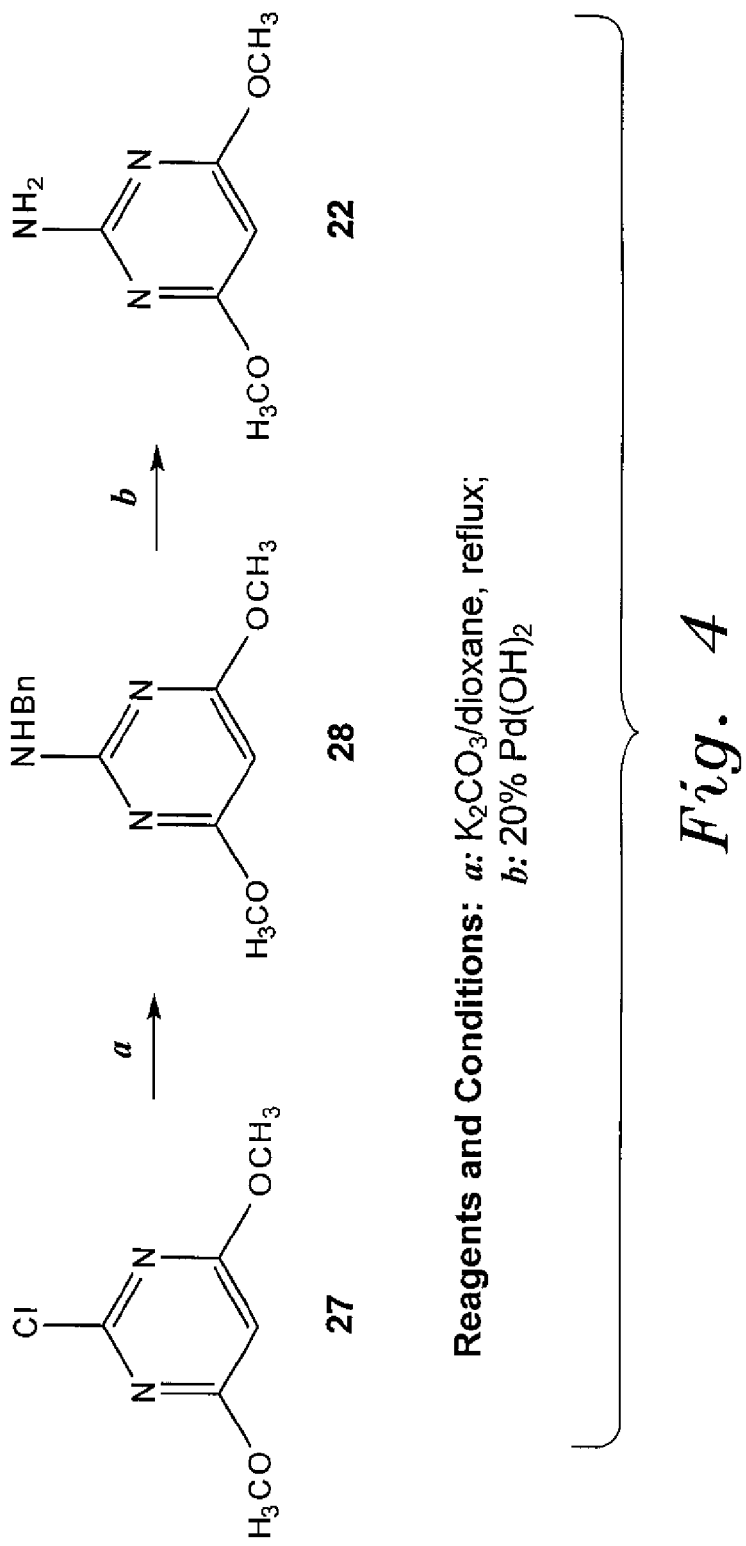
FIG. 4 is a reaction scheme showing the synthesis of the 2-aminopyrimidine intermediate compound number 22 referenced in FIG. 3.

Referring to FIG. 3, to 42.0 g (0.42 mol) of succinic anhydride (17) dissolved in 300 mL of toluene was added 20 g (0.21 mol) of 2-aminopyrimidine (21), (0.21 mol) dissolved in 200 mL of acetone, and the mixture was heated to 85° C. for 3 days. After cooling to r.t. (room temperature), the product precipitated and was filtrated and washed with toluene. The filtrate was dried in vacuo, and the dried product was then dissolved in 300 mL of anhydrous Ac$_2$O and again heated to 85° C. for 3 hrs. After removal of the remaining Ac$_2$O under vacuum, the product was purified by silica gel column chromatograph with CHCl$_3$ and recrystallized from EtOAc to give HK-1 as a white solid, mp 148.5-149.5° C. in 32% yield. $^1$H NMR (CDCl$_3$) δ 8.92 (d, J=4.88 Hz, 2H), 7.42 (t, J=4.88 Hz, 1H), 2.96 (s, 4H); Anal. Calcd for C$_8$H$_7$N$_3$O$_2$; C, 54.24; H, 3.98; N, 23.72. Found: C, 54.29; H, 4.19; N, 23.90.

Substituting compound 22 for compound 21, HK-3 was obtained as a white solid, mp 166.9-168.7° C., in 60% yield. $^1$H NMR (CDCl$_3$) δ 6.09 (s, 1H), 3.94 (s, 6H), 2.92 (s, 4H); Anal. Calcd for C$_{10}$H$_{11}$N$_3$O$_4$; C, 50.63; H, 4.67; N, 17.71. Found: C, 50.78; H, 4.80; N, 17.80.

Substituting Compound 18 for Compound 17 in the scheme for HK-1, HK-5 was obtained as a white solid, mp 220.8-221.3° C., in 51% yield. $^1$H NMR (CDCl$_3$) δ 8.88 (d, J=4.88 Hz, 2H), 7.40 (t, J=4.88 Hz, 1H), 2.83 (t, J=4.59 Hz, 4H), 2.18-2.15 (m, 2H); Anal. Calcd for C$_9$H$_9$N$_3$O$_2$; C, 56.54; H, 4.74; N, 21.98. Found: C, 56.77; H, 4.85; N, 21.70.

Substituting Compound 18 for Compound 17 and Compound 22 for Compound 21 in the scheme for HK-1, HK-7 was obtained as a white solid, mp 229.2-232.4° C., in 63% yield. $^1$H NMR (CDCl$_3$) δ 6.06 (s, 1H), 3.92 (s, 6H), 2.79 (t, J=6.59 Hz, 4H), 2.15-2.12 (m, 2H): Anal. Calcd for C$_{11}$H$_{13}$N$_3$O$_4$; C, 52.59; H, 5.22; N, 16.73. Found: C, 52.60; H, 5.40; N, 16.63.

By reaction of Compound 17 with Compound 19, as shown in FIG. 3, Compound 23, purified by silica gel column chromatography using 100:1 CHCl$_3$:MeOH as eluent, was obtained as a white solid in 86% yield. $^1$H NMR (CDCl$_3$) δ 8.57 (s, 2H), 7.44-7.43 (m, 5H), 5.21 (s, 2H), 2.93 (s, 4H).

By reaction of Compound 18 with Compound 19, as shown in FIG. 3, Compound 24, purified with silica gel column chromatography using 100:1 CHCl$_3$:MeOH as eluent, was obtained as a white solid in 70% yield. $^1$H NMR (CDCl$_3$) δ 8.54 (s, 2H), 7.44-7.39 (m, 5H), 5.19 (s, 2H), 2.81 (t, J=6.59 Hz, 4H), 2.17-2.13 (m, 2H).

By reaction of Compound 17 with Compound 20, as shown in FIG. 3, Compound 25, purified by silica gel column chromatography with 100:1 CHCl$_3$:MeOH as eluent, was obtained as a white solid in 73% yield. $^1$H NMR (CDCl$_3$) δ 7.44-7.31 (m, 5H), 5.07 (s, 2H), 3.96 (s, 6H), 2.28 (s, 4H).

By reaction of Compound 18 with Compound 20, as shown in FIG. 3, Compound 26, purified with silica gel column chromatography with 100:1 CHCl$_3$:MeOH as eluent, was obtained as a white solid in 63% yield. $^1$H NMR (CDCl$_3$) δ 7.47-7.35 (m, 5H), 5.03 (s, 2H), 3.96 (s, 6H), 2.80 (t, J=6.59 Hz, 4H), 2.15-2.13 (m, 2H).

Example 4

Synthesis of HK-2, HK-4, HK-6, and HK-8

The following describes the general synthesis of 1-(5-hydroxy-2-pyrimidyl)pyrrolidine-2,5-dione (HK-2), 1-(4,6-dimethox-5-hydroxy-2-pyrimidyl)pyrrolidine-2,5-dione (HK-4), 1-(5-hydroxy-2-pyrimidyl)piperidine-2,6-dione (HK-6), and 1-(4,6-dimethoxy-5-hydroxy-2-pyrimidyl)piperidine-2,6-dione (HK-8).

Referring to the reaction scheme of FIG. 3, Compound 23 (14.7 g, 51.9 mmol) dissolved in 750 mL of acetone was hydrogenated with 3.7 g of 10% Pd/C catalyst at r.t for 12 hrs. After filtration and solvent evaporation, HK-2 was obtained as a white fluffy solid. Following recrystallization with i-PrOH, 10 g of HK-2, mp 278.0-280.0° C., was obtained in 76% yield. $^1$H NMR (DMSO-d$_6$) δ 11.02 (s, 1H), 8.46 (s, 2H), 2.85 (s, 4H): Anal. Calcd for C$_8$H$_7$N$_3$O$_3$; C, 49.74; H, 3.65; N, 21.75. Found. C, 50.00; H, 3.69; M, 21.54.

Substituting Compound 25 for Compound 23 in the synthesis of HK-1, HK-4 was obtained as a white solid, mp 193.7-195.0° C., in 91% yield after recrystallization from Et$_2$O. $^1$H NMR (CDCl$_3$) δ 5.15 (s, 1H), 4.03 (s, 6H), 2.91 (s, 4H); Anal. Calcd for C$_{10}$H$_{11}$N$_3$O$_5$; C, 47.43; H, 4.38; N, 16.59. Found: C, 47.53; H, 4.48; N, 16.58.

Substituting Compound 24 for Compound 23 in the synthesis of HK-1, HK-6 was obtained as a white solid, mp 243.5-244.3° C., in 89% yield after recrystallization from acetone. $^1$H NMR (DMSO-d$_6$) δ 10.85 (s, 1H), 8.39 (s, 2H), 2.75 (t, J=6.35 Hz, 4H), 1.99-1.96 (m, 2H); Anal. Calcd for C$_9$H$_9$N$_3$O$_3$; C, 52.17; H, 4.38; N, 20.28 Found C, 52.14; H, 4.52; N, 20.04.

Substituting Compound 26 for Compound 23 in the synthesis of HK-1, HK-8 was obtained as a white solid, mp 222.0-224.0° C., in 86% yield after recrystallization from Et$_2$O. $^1$H NMR (CDCl$_3$) δ 6.06 (s, 1H), 3.92 (s, 6H), 2.80 (t, J=6.59 Hz, 4H), 2.15-2.13 (m, 2H); Anal. Calcd for C$_{11}$H$_{13}$N$_3$O$_5$; C, 49.44; H, 4.90; N, 15.72. Found: C, 49.52; H, 4.99; N, 15.65.

Example 5

Synthesis of HK-9, HK-11, HK-13 and HK-15

The following describes the general synthesis of 2-(pyrrolidine-1-yl)pyrimidine (HK-9), 4,6-dimethoxy-2-(pyrrolidine-1-yl)pyrimidine, HK-11, 2-(piperidine-1-yl)pyrimidine (HK-13), 4,6-dimethoxy-2-(piperidine-1-yl)pyrimidine (HK-15), 5-benzyloxy-2-(pyrrolidine-1-yl)pyrimidine (Compound 35), 5-benzyloxy-2-(piperidine-1-yl)pyrimidine (Compound 36), 5-benzyloxy-4,6-dimethoxy-2-(pyrrolidine-1-yl)pyrimidine (Compound 37), and 5-benzyloxy-4,6-dimethoxy-2-(piperidine-1-yl)pyrimidine (Compound 38).

Figure 5:
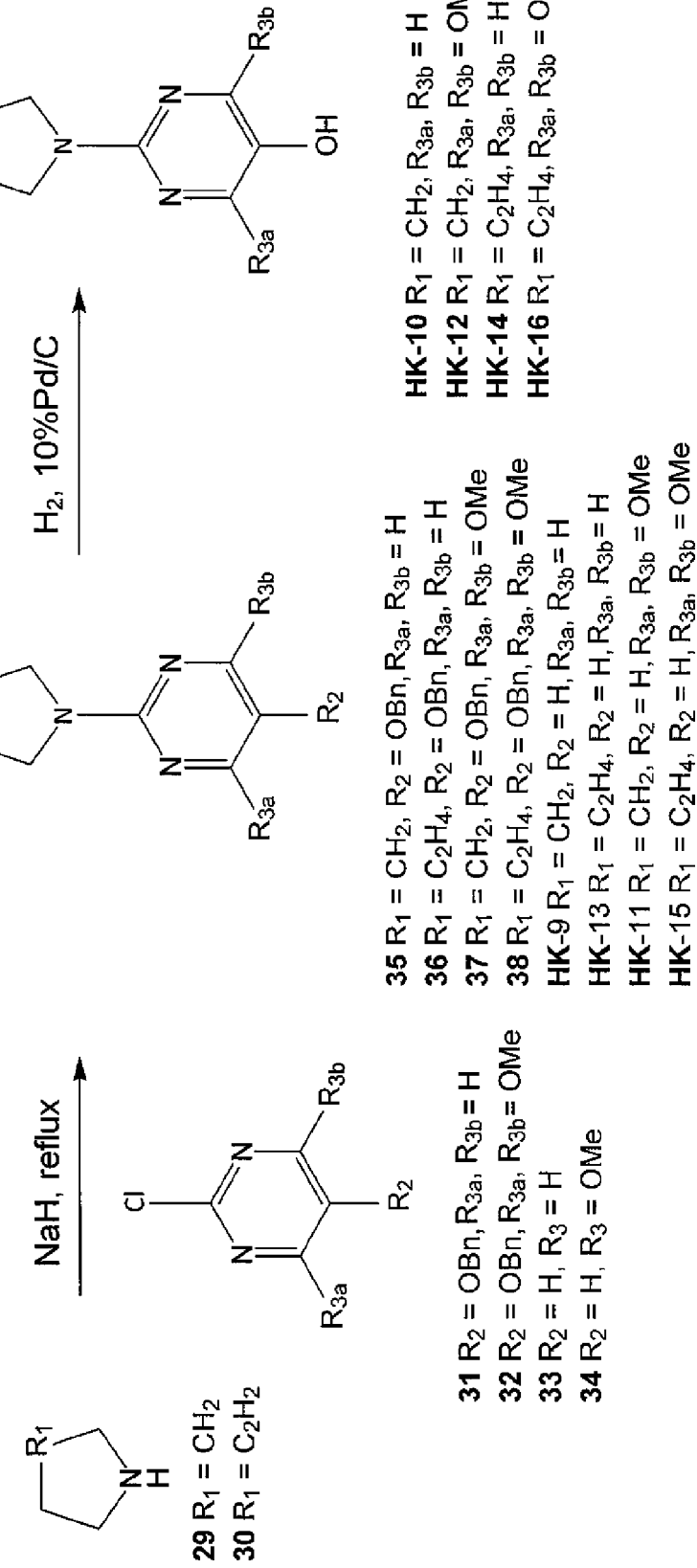
FIG. 5 is a reaction scheme showing the synthesis of the neuroprotective monofunctional antioxidants and their parent compounds HK-9 to HK-16 according to the present invention.

Referring to the reaction scheme of FIG. 5, to 9.53 mL (116 mmol) pyrrolidine (29) in 400 mL of anhydrous THF was added 2.78 g of sodium hydride (116 mmol) and the mixture was refluxed for 0.5 hr. After cooling to r.t., 12 g (105 mmol) of 2-chloropyrimidine (33) was added dropwise and the mixture was refluxed for 2 days and then cooled in an ice bath. Water (200 mL) was then added to the cooled reaction mixture and the THF was removed in vacuo. The aqueous residue was extracted with $CHCl_3$ and the combined $CHCl_3$ extracts were washed with brine, dried over magnesium sulfate, and filtered. After removal of solvent in vacuo, the residue was purified by silica gel column chromatography using 20:1 hexanes:EtOAc as eluent. The product was then recrystallized from diethyl ether ($Et_2O$) to give a 12.0 g (76%) of HK-9 as a yellow solid, mp 39.0-39.6° C. $^1$H NMR ($CDCl_3$) δ 8.31 (d, J=4.88 Hz, 2H), 6.45 (t, J=4.88 Hz, 1H), 3.57 (t, J=4.4 Hz, 4H), 2.01-1.98 (m, 4H). Anal. Calcd for $C_8H_{11}N_3$; C, 64.40; H, 7.43; N, 28.16. Found: C, 64.42; H, 7.53; N, 27.97.

Substituting Compound 34 for Compound 33 in the synthesis of HK-9, HK-11 was obtained as a white solid, mp 63.3-63.7° C., 71% yield after recrystallization from $Et_2O$. $^1$H NMR ($CDCl_3$) δ 5.34 (s, 1H), 3.87 (s, 6H), 3.56 (t, J=6.59 Hz, 4H), 1.93-1.96 (m, 4H); Anal. Calcd for $C_{10}H_5N_3O_2$; C, 57.40; H, 7.23; N, 20.08. Found: C, 57.20; H, 7.03; N, 19.91.

Substituting Compound 30 for Compound 29 in the synthesis of HK-9, HK-13 was obtained as a colorless oil in 90% yield after vacuum distillation at 90° C. under 0.25 mmHg. $^1$H NMR ($CDCl_3$) δ 8.22 (d, J=4.64 Hz, 2H), 6.35 (t, J=4.64 Hz, 1H), 3.71 (t, J=5.37 Hz, 4H), 1.64-1.58 (m, 2H), 1.56-1.51 (m, 4H); Anal. Calcd for $C_9H_{13}N_3$; C, 66.23; H, 8.03; N, 25.74. Found: C, 66.49; H, 7.95; N, 25.81.

Substituting Compound 30 for Compound 29 and Compound 34 for Compound 33 in the synthesis of HK-9, HK-15 was obtained as a white solid mp 59.8-60.4° C. in 74% yield. $^1$H NMR ($CDCl_3$) δ 5.25 (s, 1H), 3.77 (s, 6H), 3.68 (t, J=5.49 Hz, 4H), 1.60-1.55 (m, 2H), 1.52-1.48 (m, 4H); Anal. Calcd for $C_{11}H_{17}N_3O_2$; C, 59.17; H, 7.67; N, 18.82. Found: C, 58.94; H, 7.49; N, 18.56.

By reaction of Compound 29 with Compound 31, as shown in FIG. 5, Compound 35 was obtained in 86% yield. $^1$H NMR ($CDCl_3$) δ 8.06 (s, 2H), 7.34-7.25 (m, 5H), 4.93 (s, 2H), 3.45 (t, J=6.59 Hz, 4H), 1.58-1.52 (m, 6H).

By reaction of Compound 30 with Compound 31, as shown in FIG. 5, Compound 36 was obtained in 75% yield. $^1$H NMR ($CDCl_3$) δ 8.04 (s, 2H), 7.33-7.25 (m, 5H), 4.94 (s, 2H), 3.63 (t, J=4.88 Hz, 4H), 1.93-1.90 (m, 4H).

By reaction of Compound 29 with Compound 32, as shown in FIG. 5, Compound 37 was obtained in 80% yield. $^1$H NMR ($CDCl_3$) δ 7.47-7.32 (m, 5H), 4.84 (s, 2H), 3.90 (s, 6H), 3.51 (t, J=6.59 Hz, 4H), 1.95-1.92 (m, 4H).

By reaction of Compound 30 with Compound 32, as shown in FIG. 5, Compound 38 was obtained in 75% yield. $^1$H NMR ($CDCl_3$) δ 7.46-7.27 (m, 5H), 4.85 (s, 2H), 3.89 (s, 6H), 3.69 (t, J=5.49 Hz, 4H), 1.66-1.57 (m, 6H).

Example 6

Synthesis of HK-10, HK-12, HK-14 and HK-16

The following describes the general procedure of preparation of 5-hydroxy-2-(pyrrolidine-1-yl)pyrimidine (HK-10), 5-hydroxy-4,6-dimethoxy-2-(pyrrolidine-1-yl)pyrimidine (HK-12), 5-hydroxy-2-(piperidine-1-yl)pyrimidine (HK-14), and 5-hydroxy-4,6-dimethoxy-2-(piperidine-1-yl)pyrimidine (HK-16).

Referring to the reaction scheme of FIG. 5, hydrogenation of compound 38 (17.6 g, 53.4 mmol) dissolved in 350 mL of acetone with 4.4 g of 10% Pd/C catalyst at r.t. for 12 hrs gave after filtration and solvent evaporation HK-16 as a pale red solid. Recrystallization from $Et_2O$ gave 12.7 g (80%) of HK-16, mp 120.1-120.5° C. $^1$H NMR (DMSO-$d_6$) δ 7.63 (brs, 1H), 3.81 (s, 6H), 3.59 (t, J=5.25 Hz, 4H), 1.60-1.56 (m, 2H), 1.52-1.47 (m, 4H); Anal. Calcd for $C_{11}H_{17}N_3O_3$; C, 55.22; H, 7.16; N, 17.56. Found: C, 55.15; H, 7.21; N, 17.48.

Substituting compound 37 for compound 38 as shown in FIG. 5, HK-12 was obtained as a yellow solid, mp 108.7-109.2° C., in 78% yield after recrystallization from $Et_2O$. $^1$H NMR (DMSO-$d_6$) δ 7.49 (brs, 1H), 3.82 (s, 6H), 3.41 (t, J=6.47 Hz, 4H), 1.89-1.86 (m, 4H); Anal. Calcd for $C_{10}H_{15}N_3O_3$; C, 53.32; H, 6.71; N, 18.66. Found: C, 53.51; H, 6.80; N, 18.80.

Substituting compound 35 for compound 38, as shown in FIG. 5, HK-10 was obtained as a pale yellow solid, mp 151.5-151.8° C. in 84% yield after recrystallization from $Et_2O$. $^1$H NMR ($CDCl_3$) δ 8.05 (s, 2H), 3.55-3.75 (m, 4H), 1.96-1.92 (m, 4H). Anal. Calcd for $C_8H_{11}N_3O$; C, 58.17; H, 6.71; N, 25.44. Found: C, 57.92; H, 6.67; N, 25.18.

Substituting compound 36 for compound 38 as shown in FIG. 5, HK-14 was obtained as a pale red solid, mp 94.3-94.7° C., in 79% yield after recrystallization from $Et_2O$. $^1$H NMR ($CDCl_3$) δ 8.06 (s, 2H), 3.47 (t, J=6.59 Hz, 4H), 1.70-1.40 (m, 6H). Anal. Calcd for $C_9H_{13}N_3O$; C, 60.32; H, 7.31; N, 23.45. Found: C, 60.15; H, 7.25; N, 23.26.

Example 7

Synthesis of 5-amino-2-chloropyrimidine

Compound 40

Figure 6:
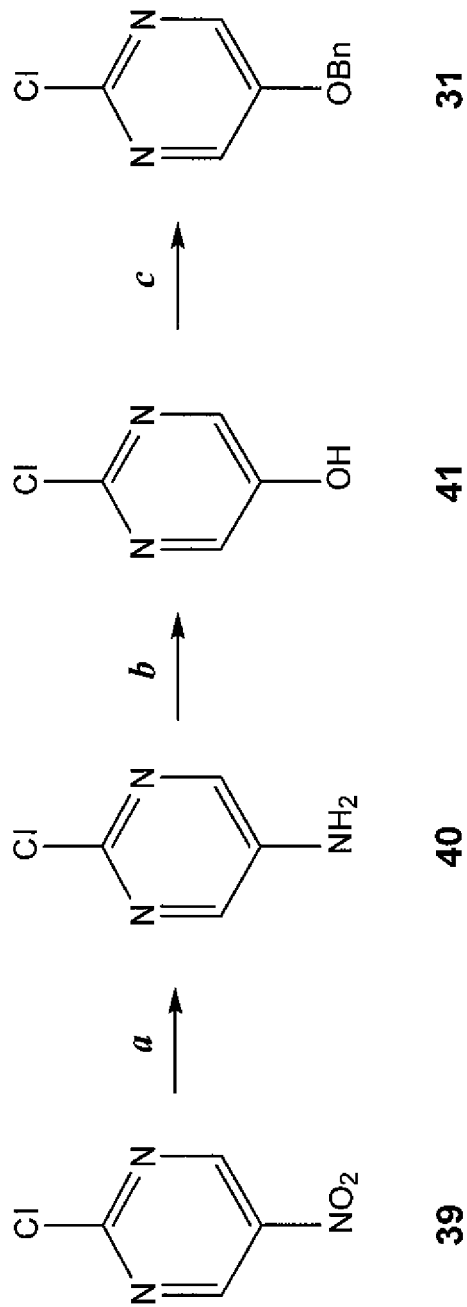
FIG. 6 is a reaction scheme showing the synthesis of intermediates for the synthesis of HK-10 and HK-14 compounds referenced in FIG. 2B and FIG. 2F.

Referring to the reaction scheme of FIG. 6, to 140 g (0.88 mol) of 2-chloro-5-nitropyrimidine (39) dissolved in 700 mL of EtOH was added a mixture of 1400 mL of acetic acid, 700 mL water and 197 g of iron powder (70 m mesh, <212 μm). The mixture was heated overnight at 70° C. and then cooled to r.t. and then filtered. EtOH was removed from the filtrate in vacuo, and the pH was adjusted to 8 with 12 N NaOH and the product was extracted overnight with continuous liquid-liquid extraction with EtOAc. The resulting filter cake was washed with EtOAc, and the combined EtOAc layers were washed with water, then brine, dried over magnesium sulfate, and filtered. After removal of the solvent in vacuo and recrystallization with EtOH, 97.2 g (85%) of pale brown solid product 39 was obtained. $^1$H NMR (DMSO-$d_6$) δ 8.94 (s, 2H), 5.77 (brs, 2H).

Example 8

Synthesis of 2-chloropyrimidine-5-ol

Compound 41

Referring to the reaction scheme of FIG. 6, Compound 40 (40 g, 0.31 mol) in 2N sulfuric acid was refluxed for 2 hrs.

After cooling to r.t., the reaction mixture was extracted with EtOAc using continuous overnight liquid-liquid extraction. The combined EtOAc layers were washed with brine, dried over magnesium sulfate, and filtered. After solvent removal in vacuo and recrystallization with EtOH, 10 g (25%) yellow solid 41 was obtained. $^1$H NMR (DMSO-$d_6$) δ 10.93 (brs, 1H), 6.45 (t, J=4.88 Hz, 1H), 3.57 (t, J=4.4 Hz, 4H), 2.01-1.98 (m, 4H).

Example 9

Synthesis of 2-chloro-5-benzyloxy-pyrimidine

Compound 31

Referring to the reaction scheme of FIG. 6, potassium carbonate (11.6 g, 84.3 mmol) was added to 10 g of the alcohol 40 (76.6 mmol) in 500 mL of MeOH, followed by benzyl bromide (10.1 mL, 84.3 mmol). After 14 hrs stirring at r.t., the reaction was stopped by addition of water (300 mL). MeOH was evaporated and the remaining aqueous layer was extracted with CHCl$_3$. The combined CHCl$_3$ layers were washed with brine, dried over magnesium sulfate, and filtered. Removal of the solvent followed by silica gel chromatography using 100:1 CHCl$_3$:MeOH as eluent gave 15 g (89%) of 2-amino-5-benzyloxy-pyrimidine (31) as a white solid. $^1$H NMR (CDCl$_3$) δ 8.27 (s, 2H), 7.37-7.30 (m, 5H), 5.09 (s, 2H).

Example 10

Metal Attenuation—Chelation Activity

Compounds HK-1 to HK-8 readily form complexes with the redox-active metals $Cu^{1+}$, $Cu^{2+}$, $Fe^{2+}$, $Fe^{3+}$ and $Zn^{2+}$, but not with $Ca^{2+}$ or $Mg^{2+}$ (FIG. 7). The stoichiometry, determined using the method of continuous variation (job plots), was similar to that observed for the multifunctional JHX-compounds. Several solutions of each compound and the metal ion of interest were prepared at a constant total concentration of HK 1 to HK-8 and ion, but with a different mole fraction of one component. After equilibration, the change in maximum absorbance for each compound was recorded as a function of the mole fraction of the metal ion. Two linear dependences were obtained, one at a low mole fraction of metal ion and the other at a high mole fraction. The mole fraction at which the trend lines intersected (or lack thereof) was calculated to find the stoichiometric ratio. This process was repeated in triplicate for all compounds with all of the aforementioned ions. The results, summarized for series HK-1-HK-8 in FIG. 7, show that the compounds bind metal in either a 1:2 or 2:1 ratio, with no interaction with either magnesium or calcium.

Example 11

Cell Culture Studies

The MFAOs and their monofunctional analogs were examined for their ability to reduce ROS generated by peroxide, hydroxyl, and superoxide radicals by Cell Viability Studies, Superoxide Assay, and LIVE/DEAD® Viability/Cytotoxicity Assay as follows.

The in vitro cell viability studies were conducted as previously described using SH-SY5Y neuroblastoma cells (ATCC) and cultured according to ATCC procedures in 1:1 Eagles minimum essential medium with Earle's balanced salt solution and Ham's F12 (EMEM-F12) media containing (10% fetal bovine serum (FBS)) at 37° C. under a 5% $CO_2$ atmosphere. Cell viability studies were conducted over a 24 hour period in 96-well plates using the Cell Titer 96® Aqueous One Solution Cell Proliferation Assay (MTS, Promega, Madison, Wis.) with 1 mM of each compound or clioquinol (PBT1) dissolved in 0.16% DMSO. Clioquinol was purchased from TCI (98%, Tokyo, Japan) and further purified by recrystallization. This is a colorimetric method for determining the number of viable cells in proliferation or cytotoxicity assays where the One Solution contains MTS (3-(4,5-dimethylthiazol-2-yl)-5-(3-carboxymethoxyphenyl)-2-(4-sulfophenyl)-2H-tetrazolium), in the presence of phenazine methosulfate (PMS). The MTS compound is bioreduced by cells into a colored formazan product and, as measured by the amount of 490 nm absorbance, is directly proportional to the number of living cells in culture. Compared to DMSO treated cells, 24 hr cell viability decreased approximately 20%, when exposed to Trolox, for the lead 5-membered HK-2 and HK-4, and the 6-membered HK-6, but a 30% decrease was observed with HK-8. Exposure to clioquinol resulted in the largest (50%) decrease in cell viability. The protective effect of these compounds against $H_2O_2$ and hydroxyl radical generated by the Fenton reaction were examined. In the absence of oxidant, a similar decrease in cell viability was also observed with clioquinol. However, this effect was not as pronounced in the presence of an oxidant. When exposed to $H_2O_2$ alone, oxidative damage was reduced in all treated cells, and an increase in viability was observed compared to the untreated cells (DMSO and $H_2O_2$ alone). In the Fenton reaction, viability in clioquinol-treated cells was lower than DMSO control, indicating no drug effect, in addition to the inherent toxicity of clioquinol at the concentration used.

The ability of the HK series of multifunctional and monofunctional antioxidant compounds to specifically reduce superoxide radicals in live cells was assessed in both SH-SY5Y neuroblastoma cells and ARPE-19 retinal pigmented epithelial cells. The production of superoxide by mitochondria was visualized with fluorescence microscopy using the MitoSOX™ Red reagent (Invitrogen Life Sciences, Grand Island, N.Y.), which permeates live cells, where it selectively targets mitochondria. It is rapidly oxidized by superoxide, but not by other reactive oxygen species (ROS) and reactive nitrogen species (RNS). The oxidized product is highly fluorescent upon binding to nucleic acid. For these studies, cells were seeded into 96-well plates and grown in standard media (1:1 Eagles minimum essential medium with Earle's balanced salt solution and Ham's F12 (EMEM-F12) media containing (10% fetal bovine serum (FBS)) for the human SH-SY5Y neuroblastoma cells, or Dulbecco's Modified Eagle Medium (DMEM) containing 4% FBS for the human ARPE-19 retinal pigmented epithelial cells) at 37° C. under a 5% $CO_2$ atmosphere until 80% confluence was achieved (ca. 24 hr). The cell media was then removed from each well, and the wells were washed with PBS. Compounds (HK series and JHX series and antioxidant standards (Hydroquinone (HQ), Trolox (T), Vitamin E (VE), Vitamin C (VC)) dissolved in DMSO (10 μL) were then added to each well, along with fresh media (140 μL) without serum albumin (FBS). Superoxide dismutase (SOD, 500 μg/mL, 10 μL) was used as an additional control, and cells in all groups (controls, drug treated, and SOD treated groups) were exposed to the same amounts of DMSO. After addition, the cells were incubated at 37° C. under a 5% $CO_2$ atmosphere for 1 hr. Xanthine oxidase (XO), was then added (25 mU/mL) to generate approximately 100 μM superoxide, and culture continued for an additional hour. The media was then again removed, and the cells were washed with PBS. Finally, the cells were stained with 100 µL of the MitoSOX Red reagent (5 µM), and 2 hr after further incubation, the fluorescence of each well was measured using fluorescent microplate reader at Ex/Em=510/580 nm.

The generation of superoxide under these experimental conditions was reduced by both antioxidants. The protective multifunctional antioxidants were examined in a dose-dependent manner in both SH-SY5Y neuroblastoma cells and ARPE-19 retinal pigmented epithelial cells. In the SH-SY5Y neuroblastoma cells HK-2, HK-4 and clioquinol demonstrated similar reduction of superoxide radical, while compounds HK-9 and HK-11 (analogs not possessing the required hydroxyl group) had no effect in reducing the superoxide anion radical. Monofunctional antioxidants HK-10, HK-12, HK-14 and HK-16 also demonstrated protection, while the monofunctional chelators HK-1, HK-3, HK-5 and HK-7 did not. In ARPE-19 retinal pigmented epithelial cells, clioquinol and the MFAOs HK-2, HK-4 and JHX-4, along with the antioxidant Trolox, show similar dose-dependent reduction of superoxide anion radical.

The ability of the HK series of multifunctional antioxidant compounds to specifically protect against hydroxyl radical-induced cell death was assessed in both SH-SY5Y neuroblastoma cells and ARPE-19 retinal pigmented epithelial cells using the LIVE/DEAD® Viability/Cytotoxicity Assay (Invitrogen Life Sciences, Grand Island, N.Y.). The cells were seeded into 96-well plates and grown in standard media (1:1 EMEM-F12 media containing 10% FBS for the human SH-SY5Y neuroblastoma cells, or DMEM containing 4% FBS for the human ARPE-19 retinal pigmented epithelial cells), at 37° C. under a 5% $CO_2$ atmosphere until 80% confluence was achieved (ca. 24 hr). The media was then removed, and the cells were washed with PBS. Compounds (HK series and JHX series or antioxidant standards (Hydroquinone (HQ), Trolox (T), Vitamin E (VE), Vitamin C (VC)) dissolved in DMSO (10 µL) were again added to the cells, along with the appropriate media without FPS. Following a 1 hr incubation at 37° C. under a 5% $CO_2$ atmosphere, Fenton reagents ($Fe^{2+}$ and hydrogen peroxide dissolved in appropriate media without FBS to give a final concentration of 100 µM) were added to each well, and incubation continued. After 2 hr of incubation with Fenton reagent, the media was removed and the cells were washed with PBS. The cells were stained with 100 µL of the LIVE/DEAD reagent containing calcein AM (AM, 8 µM for NB) and ethidium homodimer-1 (EthD-1, 16 µM for NB) for 1 hr at 37° C. The fluorescence of each well was measured using a fluorescent microplate reader at Ex/Em=494/517 nm (Fsam for LIVE Cells) and Ex/Em=528/617 nm (Fsam for DEAD Cells). The fluorescence of control samples was also measured as follows: Fmax for LIVE Cells (The fluorescence at Ex/Em=494/517 nm in live cells samples labeled with AM only); Fmin for LIVE Cells (The fluorescence at Ex/Em=494/517 nm in live cells samples labeled with EthD-1 only); Fmax for DEAD Cells (The fluorescence at Ex/Em=528/617 nm in dead cells samples labeled with EthD-1 only); Fmin for DEAD Cells (The fluorescence at Ex/Em=528/617 nm in dead cells samples labeled with AM only); Blank 494/517 (The fluorescence at Ex/Em=494/517 nm without dye and cells); Blank 528/617 (The fluorescence at Ex/Em=528/617 nm without dye and cells). For the dead cells control, the cells were incubated with 70% of ethanol for 30 min at 37° C. The percentage of live cells was calculated from the fluorescence readings using the equation $$\% \text{ LIVE Cells} = \frac{(F_{sem \text{ for LIVE Cells}} - \text{Blank}_{494/517}) - (F_{min \text{ for LIVE Cells}} - \text{Blank}_{494/517})}{(F_{max \text{ for LIVE Cells}} - \text{Blank}_{494/517}) - (F_{min \text{ for LIVE Cells}} - \text{Blank}_{494/517})} \times 100\%$$

The percentage of dead cells was calculated from the fluorescence readings using the equation:

$$\% \text{ DEAD Cells} = \frac{(F_{sem \text{ for DEAD Cells}} - \text{Blank}_{528/617}) - (F_{min \text{ for DEAD Cells}} - \text{Blank}_{528/617})}{(F_{max \text{ for DEAD Cells}} - \text{Blank}_{528/617}) - (F_{min \text{ for DEAD Cells}} - \text{Blank}_{528/617})} \times 100\%$$

The results obtained with the LIVE/DEAD® Viability/Cytotoxicity assay were complementary with similar dose-dependent increase in live cells, and reduction in dead cells was observed with both the multifunctional antioxidant compounds and antioxidant standards. One 2 hour exposure to hydroxyl radicals generated by 1 mM Fenton reagent in both SH-SY5Y neuroblastoma cells and ARPE-19 retinal pigmented epithelial cells caused a reduction in live cells and an increase in dead cells. In SH-SY5Y neuroblastoma cells, the MFAOs HK-2 and HK-4, as well as multifunctional chelators HK-10, HK-12, HK-14 and HK-16, along with clioquinol, have a similar dose-dependent protection against 2 hours exposure to hydroxyl radicals, while compounds HK-9 and HK-11 (analogs not possessing the required hydroxyl group) had no effect in protecting the cells. In ARPE-19 retinal pigmented epithelial cells, the antioxidant, along with the MFAOs HK-2, HK-4 and JHX-4 and clioquinol, shows similar dose-dependent protection against 2 hours exposure to hydroxyl radical. Monofunctional antioxidants HK-10, HK-12, HK-14 and HK-16 also demonstrated dose-dependent protection.

Example 12

Mitochondrial Viability/Toxicity

The laser dye rhodamine 123 is shown to be a specific probe for the localization of mitochondria in living cells. Because of its selectivity for mitochondria, this stain can be used to probe alterations in mitochondria induced by drugs. Therefore, studies were conducted to determine whether MFAOs can adversely alter mitochondrial function through their ability chelate transition metals.

Human SH-SY5Y neuroblastoma cells were seeded into 8-well microscope plates (BD Falcon, 800µ-slides), and the cells were incubated in EMEM-F12 media containing 10% FBS at 37° C. under a 5% $CO_2$ atmosphere. Once the cells were approximately 80% confluent in each well, the media was removed and the cells were washed with PBS. The cells were then pre-incubated for 1 hour at 37° C. under a 5% $CO_2$ atmosphere with 200 µL of HBSS medium without FBS containing drug JHX-1, -4, -5, -8, HK-2, -4, -9, -11, or Clioquinol dissolved in DMSO, so that final drug concentrations of 1 mM in 4% DMSO were achieved. Then $MnCl_2$ was added to the appropriate cells groups to give a final concentration of 1 mM, and the groups were cultured for an additional 2 hours. After the 3-hour exposure to manganese, the media was removed and the cells were washed with PBS. The cells were then stained with 100 µL of the fluorescent dye rhodamine 123 (Rh123) (20 μM) and Hoechst 33342 (8 μM) per well at 37° C., 5% $CO_2$ for 30 min. Then the cells were washed 3 times for 5 min with media, and finally with sterilized HPLC grade water. Finally, the plate shelf was removed, ten microliter of cell medium containing 10% FBS was added to the each well, and the wells were covered with a rectangular cover glass. The gap between the cover glass and slide glass was sealed with nail polish, and the cells were then examined by confocal fluorescent microscopy. Similar procedures were employed for the RPE cell studies. However, the ARPE-19 RPE cells were cultured with DMEM containing 4% FBS.

Both the neuroblastoma and RPE cells examined demonstrated mitochondrial red rhodamine 123 staining, as well as the presence of DNA in the nuclei with the blue staining Hoechst 33342. No change in rhodamine staining was observed when MFAOs or their monofunctional analogs were added to the cells. However, addition of 1 mM $MnCl_2$ to these cells resulted in the loss of rhodamine staining, indicative of mitochondrial dysfunction. This loss of rhodamine 123 staining was not observed when the $MnCl_2$ was added to cells containing the MFAO analogs or clioquinol. These studies indicate that the MFAO analogs are not toxic to mitochondria. Instead, they, along with clioquinol, protect mitochondrial function by apparently complexing Mn.

Example 13

MFAOs can Alter $A\beta_{1-42}$/Zn Complexes

Aβ plaques are present in the brain, lens and retina of patients with AD. Aggregation of the peptide amyloid-beta (Aβ) to amyloid plaques is a key event in Alzheimer's disease. According to the amyloid cascade hypothesis, Aβ aggregates are toxic to neurons via the production of reactive oxygen species, and are hence directly involved in the cause of the disease. Zinc ions play an important role because they are able to bind to Aβ and influence the aggregation properties. The Alzheimer's therapeutics Clioquinol and PBT2 promote amyloid-beta degradation by releasing zinc from the complex.

The ability of MFAOs to release zinc from amyloid beta/zinc complex was investigated using $A\beta_2$ from American Peptide Company, Inc. (Vista, Calif.). The $A\beta_{1-42}$/Zn complex was prepared as follow. $ZnSO_4$ solution (200 μM) and $A\beta_{1-42}$ (200 μM) were mixed together and incubated at 37° C. After 48 hr incubation, the mixture was centrifuged at 14000× g, 3 min to pellet the aggregated $A\beta_{1-42}$. The aggregated $A\beta_{1-42}$ was then resuspended in water or 200 μM of drugs. The complex was diluted with Hank's Balanced Saline Solution (HBSS) to give a final 10 μM concentration for each component. This complex was then used in the following studies employing human SH-SY5Y neuroblastoma and ARPE-19 pigmented epithelial cells. The studies were repeated 2-4 times.

Human SH-SY5Y neuroblastoma cells were seeded into 8-well microscope plates (BD Falcon, 800μ-slides), and the cells were incubated in EMEM-F12 media containing 10% FBS at 37° C. under a 5% $CO_2$ atmosphere. Once the cells were approximately 80% confluent in each well, the media was removed, and the cells were washed with phosphate buffered saline (PBS). The cells were then pre-incubated with 200 μL of HBSS medium containing 10 μM of drug (JHX-1, -4, -5, -8, HK-2, -4, -9, -11, or Clioquinol dissolved in DMSO) without FBS for 1 hr at 37° C. under a 5% $CO_2$ atmosphere. After the 1-hour exposure to each drug, the media was exchanged with 200 μL HBSS media containing either 10 μM of $A\beta_{1-42}$/Zn/drug (1/1/1) or, for the control groups, HBSS media containing $A\beta_{1-42}$/Zn, Zn/drug, $A\beta_{1-42}$/drug, or $A\beta_{1-42}$. The cells were then further cultured for 1 hr at 37° C. under a 5% $CO_2$ atmosphere. The media was again removed, washed with PBS, and the cells were then stained with 100 μL of the fluorescent dye zinquin (10 μM) in EMEM-F12 (1:1) per well. After 30 min culture at 37° C. under a 5% $CO_2$ atmosphere, the zinquin media was removed and replaced with PBS containing 4% paraformaldehyde. The zinquin fluorescence was then measured in the fixed cells by confocal fluorescence microscopy using a DAPI (4',6-diamidino-2-phenylindole) DAPI filter set to assess the cellular compartmentalization of zinc. The studies were repeated 2-4 times.

Example 14

Bioavailability Studies

Bioavailability studies were conducted in C57BL/6 mice fed chow containing 0.05% of each drug (90 mg/kg/day average dose) for 14 days. Following whole body perfusion at the time of sacrifice, the lens, neural retina and brain were removed and analyzed by HPLC-MS. These compounds achieved significantly higher brain levels of drug compared to JHX-4 and -8. However, in contrast to the JHX series, these HK compounds failed to reach adequate levels in the lens (mean±SEM). The graphs show that all MFAOs have good oral bioavailability to at least one target tissue. With the exception of JHX-8, this was anticipated because all compounds also conformed to Lipinski's Rule of 5. Lipinski's rule states that oral bioavailability is linked to the parameters: (1) hydrogen bond donors (NH or OH)≤5; (2) hydrogen bond acceptors (N or O)≤10; (3) a molecular weight≤500; and (4) an octanol-water partition coefficient log P=log($C_{Octanol}$/$C_{water}$)≤5. JHX-8 possesses 12 hydrogen bond acceptors; nevertheless, it still demonstrates good bioavailability.

Example 15

Predicting Brain/Lens Uptake with Molecular Descriptors

Analysis of the uptake and distribution of these MFAOs to the ocular and neural tissues analyzed requires a number of complex pharmacokinetic steps. For the lens this requires crossing the blood aqueous barrier (BAB), entering the aqueous, and finally the lens by diffusion, while for the neural retina and brain, this requires crossing the blood retinal barrier (BRB) or blood-brain barrier (BBB), respectively. Although these compounds are lipophilic and are not be expected to interact with specific uptake or efflux receptors, neither the anticipated relationship between lenticular uptake and drug lipophilicity nor the anticipated similar BBB and BRB permeability relationship to lipophilicity was observed. Instead, promising regression analyses with molecular descriptors suggest that significant differences in the uptake of lipophilic MFAOs in the lens, brain and retina can be predicted by the analysis of select molecular descriptors. Physical properties of these compounds were examined.

A three-dimensional (3D) structure for each compound was generated using Molecular Operating Environment (MOE 2007.09, Chemical computing group, CO., Ltd.), and the 3D conformation was then minimized using the Hamiltonian (MMFF94X) energy minimizing program. A number of molecular descriptors were then calculated at this lowest energy conformation. These included log P, which is the logarithm of the compounds' partition coefficient between n-octanol and water, log($C_{Octanol}/C_{water}$), and describes the hydrophilicity or lipophilicity. Hydrophobic drugs with high octanol/water partition coefficients are preferentially distributed to hydrophobic compartments, such as lipid bilayers of cells, while hydrophilic drugs (low octanol/water partition coefficients) preferentially are found in hydrophilic compartments, such as blood serum. Also calculated was Topological Polar Surface Area (TPSA), which is defined as the surface sum over all polar atoms, (N, O, S), including attached hydrogens. This parameter is used to predict absorption. Molecules with a polar surface area of greater than 140 Å$^2$ are usually believed to be poor at permeating cell membranes. For molecules to penetrate BBB, TPSA should be less than 60 Å$^2$. Also calculated was: Dipole Moment (DM: $\mu$, AM1_$\mu$, MNDO_$\mu$, PM3_$\mu$), which is a measure of the electrical polarity of a system of charges on a molecule. The dipole moment of a molecule determines its polarity, and this parameter is often used in drug-receptor interaction and quantitative structure-activity relationship studies. Also calculated was Molar Refractivity (MR), which estimates the polarizability of a molecule. It is one of the oldest and most successful descriptors used in QSAR studies. MR often shows a strong correlation with ligand binding, and is complementary to log P. MR gives a measure of nonlipophilic interactions. MR is related not only to the volume of the molecules, but also to the London dispersive forces that act in the drug-receptor interaction.

Also calculated was Atomic Polarizabilities (apol), which is an estimation of the average molecular polarizability. Apol is based on the structure of the compounds, and is therefore independent of the number and type of probes used. Also calculated was: Water Accessible Surface Area (ASA), which is the molecule's surface area that is accessible to water. For Polar And Hydrophobic Surface Areas (PSA, HSA), PSA is calculated via the sum of polar region contributions, while HSA is calculated via the sum of hydrophobic region contributions. Also calculated was Charge-Weighted Negative/Positive Surface Area (CASA−/+), which is the total charge weighted partial negatively or positively charged molecular surface area. Also calculated was: Hydrophobic Volume (D), which is defined as the molecular envelope generating attractive hydrophobic interactions. Hydrophobic descriptors at eight different energy levels are adapted to the usual energy range of hydrophobic interactions (from −0.2 to −1.6 kcal/mol). Also calculated was Hydrophilic Volume (W), which describes the molecular envelope that is accessible to and attractively interacts with water molecules. W varies with the level of interaction energies. W1-W3 computed from molecular fields of −0.2 to −1.0 kcal/mol account for polarizability and dispersion forces; W4-W8 from molecular fields of −2.0 to −6.0 kcal/mol account for polar and strong H-bond donor-acceptor regions. Also calculated was Polar Volume (Wp), which is the volume of polar groups of the molecule. Also calculated was Kappa Shape Index (Kier1-3), which is a measure of the branching of a molecule and provides a measure of its steric bulk.

Also calculated was Molecular Globularity (G), which is defined as the ratio of molecular surface out of surface area of a sphere of volume, and is related to molecular flexibility. G is 1.0 for perfect spherical molecules. Also calculated was Critical Packing Parameter (CP), which defines a ratio between the hydrophilic and lipophilic part of a molecule. In contrast to the hydrophilic-lipophilic balance, CP refers just to molecular shape. It is defined as: volume (lipophilic part)/ [(surface(hydrophilic part)*(length of lipophilic part)]. Also calculated was: Topology Descriptor ($f_{MF}$), which describes the structural complexity of a compound based on the size of its molecular framework (MF) in relation to its overall size. $f_{MF}$ is defined as the fraction of the size of the molecular framework versus the size of the whole molecule. Promiscuity, defined as a molecule's ability to form non-specific multiple interaction with proteins, correlates with $f_{MF}$ when the $f_{MF}$ values are large. Individual correlations observed between each of the above physicochemical/topological descriptors and the concentration of 6 MFAOs and analogs in either lens, neural retina, and brain were shown. While the regression analysis suggest significant relations, in many cases these correlations may be artificial due to an uneven distribution of points clustered at either end of the graph (e.g. in Lens, logP, CASA−CASA+). Therefore, only graphs demonstrating a wider distribution of points were considered positive (e.g. in Lens, TPSA, DM, PSA, $f_{MF}$). Similar molecular descriptors in lens and brain gave inverse correlations, while no observed correlations were obtained with the neural retina.

Example 16

Zinquin Analysis of the Cellular Compartmentalization of Zn Exposed to Human ARPE-19 Retinal Pigmented Epithelial Cells For this study the same procedures were utilized as described for the neuroblastoma cell line, with the exception that ARPE-19 RPE cells were cultured with DMEM containing 4% FBS.

Zinquin staining, which has a blue fluorescence, shows the presence of labile zinc$^{2+}$ in the cytoplasm, and this staining disappears after $A\beta_{1-42}$/Zn complex is added to the cells, indicating that the labile zinc becomes now no longer available or that it is released from the complex. This does not occur when cells have been incubated with MFAOs or clioquinol, suggesting these compounds maintain labile zinc levels in the presence of aggregated $A\beta_{1-42}$/Zn complex. Similar effects were observed in both the neuroblastoma and RPE cell lines. Similar activity has been similarly for PBT2.

In summary, HK-2, HK-4, HK-6, and HK-8 are multifunctional neuroprotective antioxidants that both chelate transition metals that might otherwise convert nonreactive oxygen species into reactive oxygen species (ROS), and also scavenge free radicals, converting ROS into less harmful compounds. HK-1, HK-3, HK-5, and HK-7 are monofunctional neuroprotective antioxidants that chelate transition metals that might otherwise convert nonreactive oxygen species into reactive oxygen species (ROS). HK-10, HK-12, HK-14, and HK-16 are monofunctional neuroprotective antioxidants that scavenge free radicals, converting ROS into less harmful compounds. All of these compounds may be administered orally as ester prodrugs (conversion to ester prodrugs is a well-known technique in the art that introduces lipophilicity and masks hydrogen bonding groups of an active compound by addition of the ester group), and they are all shown to be capable of crossing the blood-brain barrier.

HK-2, HK-4, HK-6, and HK-8, by their ability to independently chelate such metals as Fe, Cu or Zn and to scavenge free radicals generated from different sources are neuroprotective and are beneficial for the treatment of various neurological disorders, such as Alzheimer's disease, Parkinson's disease, ALS, traumatic brain injury, ocular disorders such as cataract, glaucoma, age-related macular degeneration and other retinal degeneration, as well as reducing the progression of diabetic complications. These compounds may also be beneficial in reducing the accumulation of Fe, Cu, or Zn select diseases.

Monofunctional antioxidant chelators HK-1, HK-3, HK-5, HK-7 and their analogs, by their ability to chelate such metals as Fe, Cu or Zn, are beneficial for treating Huntington's disease and Alzheimer's disease, as well as copper poisoning or iron poisoning.

Monofunctional free radical scavengers HK-10, HK-12, HK-14, HK-16 and their analogs, by their ability to scavenge free radicals, are not only beneficial for the age-related diseases mentioned above, but also as radioprotective agents against ionizing radiation.

It is to be understood that the present invention is not limited to the embodiments described above, but encompasses any and all embodiments within the scope of the following claims.

I claim:
1. A compound having the formula:

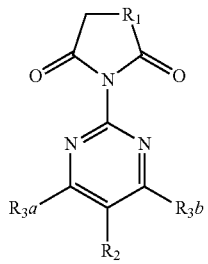

wherein $R_1$ is $CH_2$ or $C_2H_4$; $R_2$ is —$OR_4$ where $R_4$ is H, carbonylalkyl or carbonylaryl; and $R_{3a}$ and $R_{3b}$ are independently selected from the group consisting of H and —O-alkyl, and pharmaceutically acceptable salts thereof.

2. The compound according to claim 1, wherein the compound is selected from the group consisting of:

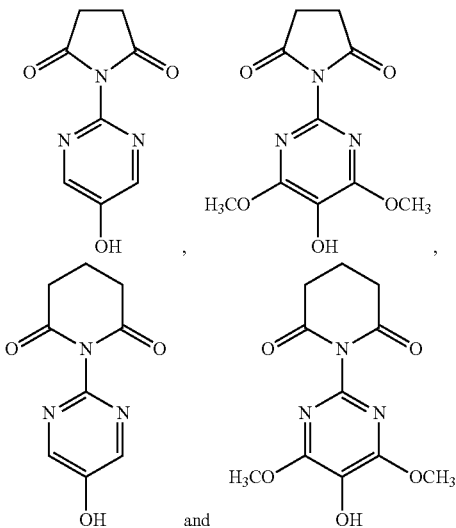

and pharmaceutically acceptable salts thereof.

3. The compound according to claim 1, wherein the compound has the formula:

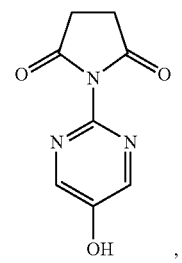

and pharmaceutically acceptable salts thereof.

4. The compound according to claim 1, wherein the compound has the formula:

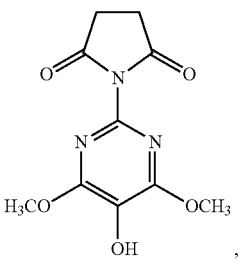 [SMILES: COc1nc(N2C(=O)CCC2=O)nc(OC)c1O]

and pharmaceutically acceptable salts thereof.

5. The compound according to claim 1, wherein the compound has the formula:

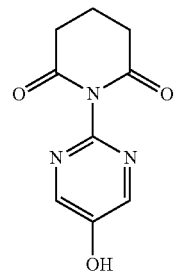

and pharmaceutically acceptable salts thereof.

6. The compound according to claim 1, wherein the compound has the formula:

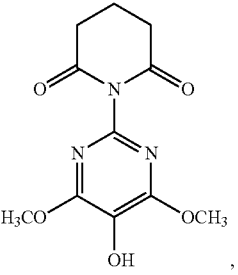

and pharmaceutically acceptable salts thereof.

7. A compound having the formula:

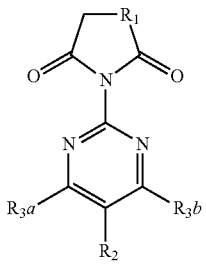

wherein $R_1$ is $CH_2$ or $C_2H_4$; $R_2$ is H; and $R_{3a}$ and $R_{3b}$ are independently selected from the group consisting of H and —O-alkyl, and pharmaceutically acceptable salts thereof provided that $R_1$ is not $CH_2$ when $R_{3a}$, and $R_{3b}$ are both H.

8. The compound according to claim 2, wherein the compound is selected from the group consisting of

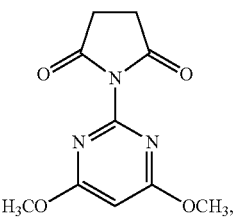 [SMILES: COc1cc(OC)nc(N2C(=O)CCC2=O)n1]

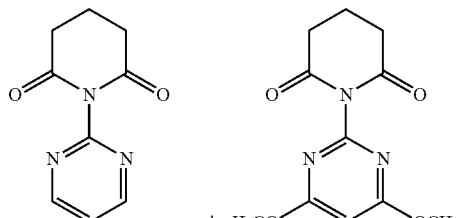

9. The compound according to claim 7, wherein the compound has the formula:

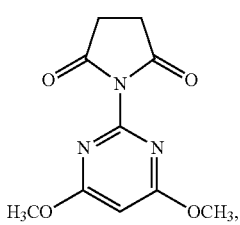

and pharmaceutically acceptable salts thereof.

10. The compound according to claim 7, wherein the compound has the formula:

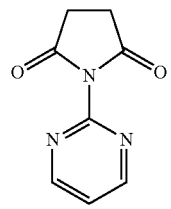

and pharmaceutically acceptable salts thereof.

11. The compound according to claim 7, wherein the compound has the formula:

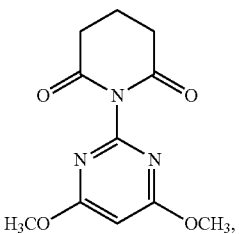

and pharmaceutically acceptable salts thereof.

12. A compound of the formula:

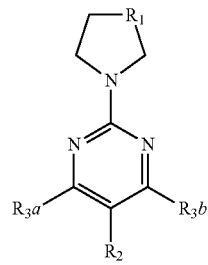

wherein $R_1$ is $CH_2$ or $C_2H_4$; $R_2$ is —$OR_4$ where $R_4$ is H, carbonylalkyl or carbonylaryl; and $R_{3a}$ and $R_{3b}$ are independently selected from the group consisting of H and —O-alkyl, provided that $R_4$ is not H when $R_{3a}$ and $R_{3b}$ are both H and $R_1$ is $C_2H_4$, and pharmaceutically acceptable salts thereof.

13. The compound according to claim 12, wherein the compound is selected from the group consisting of

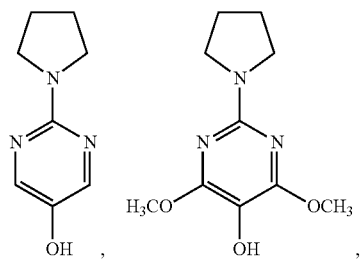

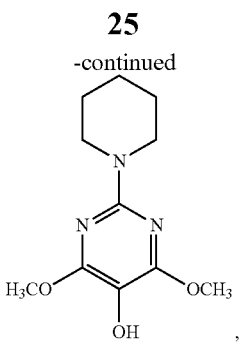
and pharmaceutically acceptable salts thereof.
* * * * *